(12) United States Patent
Fein et al.

(10) Patent No.: US 10,159,688 B2
(45) Date of Patent: Dec. 25, 2018

(54) METHODS AND COMPOSITIONS FOR ENHANCING OXYGEN LEVELS IN TISSUES

(71) Applicant: M. Alphabet 3., L.L.C., Delray Beach, FL (US)

(72) Inventors: Howard Fein, Redondo Beach, CA (US); Joshua M. Berlin, Boca Raton, FL (US)

(73) Assignee: M. ALPHABET 3, L.L.C., Delray Beach, FL (US)

( * ) Notice: Subject to any disclaimer, the term of this patent is extended or adjusted under 35 U.S.C. 154(b) by 0 days.

(21) Appl. No.: 14/776,671

(22) PCT Filed: Mar. 14, 2014

(86) PCT No.: PCT/US2014/029676
§ 371 (c)(1),
(2) Date: Sep. 14, 2015

(87) PCT Pub. No.: WO2014/145037
PCT Pub. Date: Sep. 18, 2014

(65) Prior Publication Data
US 2016/0038515 A1      Feb. 11, 2016

Related U.S. Application Data

(60) Provisional application No. 61/801,587, filed on Mar. 15, 2013.

(51) Int. Cl.
| | |
|---|---|
| *A61K 9/00* | (2006.01) |
| *A61K 9/06* | (2006.01) |
| *A61K 9/127* | (2006.01) |
| *C12N 5/071* | (2010.01) |
| *A61K 31/683* | (2006.01) |
| *A61K 31/6615* | (2006.01) |

(52) U.S. Cl.
CPC ........ *A61K 31/6615* (2013.01); *A61K 9/0014* (2013.01); *A61K 9/06* (2013.01); *A61K 9/127* (2013.01); *A61K 31/683* (2013.01); *C12N 5/0698* (2013.01)

(58) Field of Classification Search
None
See application file for complete search history.

(56) References Cited

U.S. PATENT DOCUMENTS

| | | | | |
|---|---|---|---|---|
| 4,911,929 | A | | 3/1990 | Farmer |
| 5,013,556 | A | * | 5/1991 | Woodle ................ A61K 9/1271 264/4.3 |
| 6,153,603 | A | * | 11/2000 | Siren .................. A61K 31/6615 514/102 |
| 6,251,927 | B1 | * | 6/2001 | Lai .......................... A61K 31/11 514/365 |
| 7,618,954 | B2 | * | 11/2009 | Nicolau ................ A61K 31/66 514/102 |
| 2002/0026945 | A1 | * | 3/2002 | Gomer ............... A61K 41/0057 128/898 |
| 2003/0180259 | A1 | * | 9/2003 | Brem .................. A61K 38/1866 424/93.2 |
| 2008/0241076 | A1 | * | 10/2008 | Durkee ................ A61K 9/0007 424/44 |
| 2009/0029951 | A1 | * | 1/2009 | Nicolau ............... A61K 31/661 514/143 |
| 2011/0021526 | A1 | * | 1/2011 | Deshpande ............ A61K 31/00 514/236.2 |
| 2012/0196930 | A1 | * | 8/2012 | Deshpande .......... A61K 9/0014 514/538 |

FOREIGN PATENT DOCUMENTS

| | | | |
|---|---|---|---|
| WO | WO-00/21543 | * | 4/2000 |
| WO | WO 2008/134082 A1 | | 11/2008 |

OTHER PUBLICATIONS

Ludwick Fedorko, et al., Hyperbaric Oxygen Therapy Does Not Reduce Indications for Amputation in Patients With Diabetes With Nonhealing Ulcers of the Lower Limb: A Prospective, Double-Blind, Randomized Controlled Clinical Trial, Diabetes Care, Mar. 2016; pp. 392-399, vol. 39.

Sharma Genesh N, et al., Penetration Enhancement of Medicinal Agents, International Research Journal of Pharmacy, May 2012, pp. 82-88, ISSN 2230-8407.

Iti Som, et al., Status of surfactants as penetration enhancers in transdermal drug delivery, Journal of Pharmacy and Bioallied Sciences, Jan.-Mar. 2012, pp. 4-9, vol. 4, Issue 1.

Supplementary European Search Report in European Application No. EP 14764582, dated Jul. 29, 2016, in 8 pages.

\* cited by examiner

*Primary Examiner* — Celeste A Roney
(74) *Attorney, Agent, or Firm* — Duane Morris LLP

(57) ABSTRACT

The present invention includes methods and compositions to enhance, inter alia, wound repair by administration of 2,3-biphosphoglycerate, myo-inositol trispyrophosphate, or a functional variant thereof.

21 Claims, No Drawings

METHODS AND COMPOSITIONS FOR ENHANCING OXYGEN LEVELS IN TISSUES

CROSS-REFERENCE TO RELATED APPLICATIONS

This application is a 35 U.S.C. § 371 U.S. National Phase Application of International Application No. PCT/US2014/029676, filed on Mar. 14, 2014, which claims the benefit of the filing date of U.S. Application No. 61/801,587, which was filed on Mar. 15, 2013, and each of which is incorporated herein by reference in their entirety.

FIELD OF THE INVENTION

The present invention features compositions and methods, including pharmaceutically or physiologically acceptable formulations, that can be used to treat patients who are suffering from conditions that are affected either directly or indirectly by erythrocyte function. Such conditions may be associated with hypoxia or a reduction in blood oxygen levels. Patients suffering from such conditions (e.g., a wound) can benefit from therapies designed to increase their oxygen levels. Such conditions include, but not limited to are, wounds (e.g., ulcerations, including to the skin and underlying tissue), neuropathies, infections, cerebrovascular disease, diabetes, anemia, acne, sepsis, erectile dysfunction, neurological-related conditions, alopecia, tissue grafts and tissue transplantation. More particularly, the invention includes compositions and methods related to the administration of 2,3-biphosphoglycerate or myo-inositol trispyrophosphate and/or any functional variants thereof, either alone or in combination with another (one or more) active pharmaceutical ingredient(s).

BACKGROUND

Erythrocytes transport oxygen from the lungs or gills to tissues within the body, from which they remove carbon dioxide and release it back to the lungs. Their small size allows them to move through capillaries to reach even the innermost parts of tissues to perform their function. Hemoglobin, a cytoplasmic metalloprotein that makes up about 96% of the erythrocyte's dry content (by weight), binds both oxygen and carbon dioxide to aid the transport. Differences in pH and other physiological variables facilitate binding to oxygen and carbon dioxide in the lungs and tissues, respectively. The importance of erythrocytes to humans is underscored by the fact that about a quarter of all the cells in the human body are erythrocytes. Their insufficient function leads to oxygen insufficiency, which in turn leads to various pathological conditions.

When erythrocytes cannot transport oxygen efficiently, either due to a decrease in their numbers or an abnormality affecting erythrocytes or hemoglobin, the result is anemia. The causes of anemia include a nutritional deficiency of iron (iron deficiency anemia), vitamin $B_{12}$ or folic acid (pernicious or megaloblastic anaemia), hemolysis (hereditary or acquired hemolytic anemia), certain infections (e.g. those causing jaundice or malaria), a genetic condition (e.g., sickle-cell anemia, thallasaemia, or hereditary splenocytosis), a physiological condition (e.g., renal failure), insufficient erythropoietin production, mentruation, an autoimmune disorder (e.g., pernicious anemia) or aplastic anemia. Blood loss and treatment with certain drugs can also cause anemia. Many anemias have a complex etiology.

Other conditions also cause oxygen insufficiency. Hypoxia is a medical condition caused by deprivation of an adequate oxygen supply, and it can affect the entire body or a body part. Hypoxemia is a related condition characterized by low arterial oxygen supply. These conditions may be caused by ischemia, an embolism (e.g., a thromboembolism or pulmonary embolism), heart attack, respiratory alkalosis, anemia, carbon monoxide poisoning, cyanide poisoning, or ventilation-perfusion mismatch (e.g., caused by exercise, lung disease, aging, smoking, pulmonary fibrosis, cirrhosis, hypoventilation, shunts, stroke, epilepsy, certain drugs (e.g., opiates, anaesthetics), sleep apnea, scoliosis, kyphosis, muscular weakness, or limiting external oxygen (e.g., caused by high altitude or diving).

SUMMARY OF THE INVENTION

In one aspect, the present invention provides compositions and methods of treating or preventing conditions that are affected either directly or indirectly by erythrocyte function, including hypoxia or reduced oxygen levels in the blood, and conditions in which a patient experiences hair loss. The methods include administering to the patient a pharmaceutical or physiologically acceptable composition that includes 2,3-biphosphoglycerate (2,3-BPG) or myo-inositol trispyrophosphate (myo-ITP) or a functional variant thereof. We use the term "functional variant" to refer to a derivative, metabolite, salt, or hydrate of a compound (e.g., 2,3-BPT or myo-ITP) that retains sufficient biological activity to be useful in a composition, method of treatment, or use described herein. Examples of variants are provided below. The compounds, functional variants thereof, or compositions including them may be pharmaceutically or physiologically acceptable (e.g. non-toxic at therapeutically effective dosages). In case of any doubt, where we refer to "2,3-biphosphoglycerate, myo-inositol trispyrophosphate, or a functional variant thereof," we mean 2,3-BPG or a functional variant of 2,3-BPG or myo-inositol trispyrophosphate or a functional variant of myo-inositol trispyrophosphate or any combination thereof.

In one embodiment, the method includes administering a therapeutically effective amount of 2,3-biphosphoglycerate or a functional variant thereof to enhance oxygen delivery to a bodily tissue (e.g., a peripheral tissue such as the skin or an externally accessible membrane (e.g., within the nose, mouth, throat, or covering a reproductive organ). The tissue may be one that is not normally exposed but rendered accessible in a purposeful way (e.g., in the context of a surgical procedure). Accordingly, the invention features compositions, methods, and uses for localized (e.g., topical) delivery of any compound or any combination of compounds described herein (e.g., to a wound bed or articular space).

In another embodiment, a method is provided for administering a therapeutically effective amount of 2,3-biphosphoglycerate or a functional metabolite thereof to treat one or more of the following medical conditions: skin ulcers, diabetic skin ulcers, peripheral neuropathy, sickle cell anemia, peripheral vascular disease, venous stasis, venous stasis skin ulcers, decubitus ulcers, burns, bacterial infection, fungal infection, viral infection, parasite infection, necrotizing infections, fasciitis, sepsis, ischemia, myocardial infarction, stroke, cerebrovascular disease, atherosclerosis, altitude sickness, anemia, iron deficiency anemia, thalassemia, erectile dysfunction, emphysema, asthma, cystic fibrosis, chronic lung disease, chronic obstructive pulmonary disease, pulmonary edema, photoaging, acne, chronic kidney disease, diabetes, gangrene, stroke, transient ischemic attack, angina, hypoxia, chronic skin wounds, spinal injury, nerve injury, skin grafts, tissue flaps, cyanosis, hypoxemia, respiratory distress, hypohemoglobinemia, hypoventilation, altitude sickness including high altitude pulmonary edema (HAPE) and high altitude cerebral edema (HACE), and to facilitate tissue transplantation in a patient. Several of these conditions are, or cause, an injury to the patient, particularly to the skin or another external surface (e.g., a tear, piercing, cut, abrasion, ulceration, or other break or disruption). Accordingly the compositions, methods, and uses described herein are generally applicable to wound care, and the invention encompasses compositions and methods for caring for a wound as well as use of the present compounds in the preparation of a medicament for wound care.

In another embodiment, a method is provided for administering a therapeutically effective amount of 2,3-biphosphoglycerate or a functional metabolite thereof to enhance physical performance and/or endurance in a subject.

The yet another embodiment, a method is provide for administering a therapeutically effective amount of 2,3-biphosphoglycerate or a functional metabolite thereof to treat one or more of the following medical conditions: hypoxia, hypoxemia, hair loss, alopecia, androgenetic alopecia, alopecia areata, telogen effluvium, anagen effluvium, cicatricial alopecia, and congenital forms of alopecia.

The invention is also directed to methods for administering an effective (e.g., therapeutically effective) amount of myo-inositol trispyrophosphate or a functional variant thereof to treat one or more of the following medical conditions: hair loss (e g., thinning), alopecia, androgenetic alopecia, alopecia areata, telogen effluvium, anagen effluvium, cicatricial alopecia, and congenital forms of alopecia.

In another aspect, the invention features a hydrogel, liposome, or skin substitute that includes 2,3-bisphosphoglycerate, myo-inositol trispyrophosphate, or a functional variant thereof.

DETAILED DESCRIPTION 2,3-bisphosphoglyceric acid (also referred to as 2,3-bisphosphoglycerate or 2,3-BPG, also known as 2,3-diphosphoglycerate or 2,3-DPG) is an organophosphate found in human red blood cells or erythrocytes (~5 mmol/L). Red blood cells or erythrocytes are also referred to as red blood corpuscles, haematids or erythroid cells. The primary function of erythrocytes is to distribute oxygenated blood to all of the body's tissues. Hemoglobin is the major protein component found in erythocytes and includes a heme group and iron atoms. Once the erythrocytes pass into the lungs, the oxygen molecules bind to the heme-iron complex. Oxygen readily enters the erythrocytes by diffusing across the cell membrane.

2,3-BPG contains three carbons and is an isomer of 1,3-bisphosphoglyceric acid, an intermediate in glycolysis. It is an allosteric effector that binds with a higher affinity to deoxygenated hemoglobin than to oxygenated hemoglobin, leading to the release of oxygen molecules from hemoglobin. The selective binding of 2,3-BPG leads to a stable low oxygen affinity state thereby making it harder for oxygen and hemoglobin to bind and more likely that oxygen will be released. This action is linked to an increased release of oxygen from erythrocytes to tissues or cells that are in the greatest need.

The conversion of 1,3-BPG to 2,3-BPG is catalyzed by 2,3-BPG mutase. 2,3-BPG phosphatase can then break down 2,3-BPG into 3-phosphoglycerate. 3-phosphoglycerate is also formed from 1,3-BPG as part of the "normal" glycolytic pathway. The alternative step involving the formation of 2,3-BPG to generate 3-phosphoglycerate occurs at the net expense of one ATP molecule. These steps are shown in the schematic below.

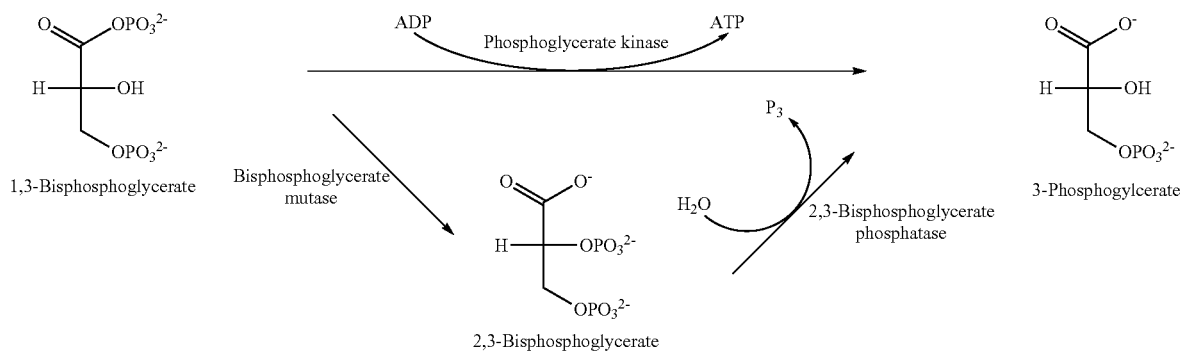

These two routes of generating 3-phosphoglycerate are important to maintain adequate concentrations of ATP required for cell metabolism and the state of hemoglobin (i.e., oxygenation vs. deoxygention states). In some conditions, there is a disturbance in this balance in order for the supply to meet the demands of the body. For example, in high altitude conditions wherein the concentration of oxygen is generally lower in cells and tissues, erythrocytes generate more 2,3-BPG in order to provide more oxygen to tissues in need. In some medical conditions such as congestive heart failure, a tendency has been observed for erythrocytes to generate increased amounts of 2,3-BPG to provide oxygen to potentially oxygen-deprived cells and tissue. Even in individuals that are acclimated to high elevation areas, higher levels of 2,3-BPG have been observed.

Diseases linked to changes in 2,3-BPG concentrations and/or metabolism include, but are not limited to are hyperthyroidism, skin ulcers, diabetic skin ulcers, peripheral neuropathy, sickle cell anemia, peripheral vascular disease, venous stasis, venous stasis skin ulcers, decubitus ulcers, burns, bacterial infection, fungal infection, viral infection, parasite infection, necrotizing infections, fasciitis, sepsis, ischemia, myocardial infarction, stroke, cerebrovascular disease, atherosclerosis, altitude sickness, anemia, iron deficiency anemia, thalassemia, erectile dysfunction, emphysema, asthma, cystic fibrosis, chronic lung disease, chronic obstructive pulmonary disease, chronic respiratory disease with hypoxia, hypoxia, pulmonary edema, photoaging, acne, chronic kidney disease, diabetes, gangrene, stroke, transient ischemic attack (TIA), angina, hypoxia, chronic skin wounds, spinal injury, nerve injury, skin grafts, tissue flaps, and tissue transplantation.

A major determinant of maximal exercise capacity and maximal performance is the delivery of oxygen to muscles. Some conditions, such as heart failure, are characterized by a reduced ability to exercise that has been linked to changes in the cardiovascular system such that the heart fails to supply an adequate amount of blood and oxygen to exercising muscles.

Similar to 2,3-BPG, administration of myo-inositol trispyrophosphate, sometimes referred to as ITPP, increases the amount of oxygen released by hemoglobin, thereby increasing the amount of oxygen delivered to cells and tissues. ITPP is a non-naturally occurring synthetic compound, derived from myo-inositol hexakisphosphate ($IP_6$), either of which can be used in the present compositions, methods, and uses. $IP_6$ is a molecule ubiquitously produced in cells that has antioxidant and anticancer properties. ITPP is considered an allosteric effector of hemoglobin, capable of crossing the cellular membranes of erythrocytes. Like 2,3-BPG, myo-ITP can be administered topically (e.g., in a gel, cream, ointment, salve, or the like) and/or placed on a substrate (e.g., a bandage, dressing, patch, or other material or device that is used to contact, cover (wholly or partially), or protect a wound). With regard to dressings, the dressing can be a foam dressing, silicone gel dressing, antimicrobial silver dressing (e.g., including nanocrystalline silver), or a hydrogel dressing. All such substrates and dressings are within the scope of the present invention.

Examples of Variants: Variants of myo-ITP include, but are not limited to: D-myo-Inositol-1,2,4,5,6-pentaphosphate (sodium salt); D-myo-Inositol-1,2,6-triphosphate (sodium salt); D-myo-Inositol-1,2-diphosphate (sodium salt); D-myo-Inositol-1,3,4,5,6-pentaphosphate (sodium salt); D-myo-Inositol-1,3,4,5-tetraphosphate (sodium salt); D-myo-Inositol-1,3,4-triphosphate (sodium salt); D-myo-Inositol-1,3,5-triphosphate (sodium salt); D-myo-Inositol-1,3-diphosphate (sodium salt); D-myo-Inositol-1,4,5,6-tetraphosphate (sodium salt); D-myo-Inositol-1,4,5-triphosphate (potassium salt); D-myo-Inositol-1,4,5-triphosphate (sodium salt); D-myo-Inositol-1,4,6-triphosphate (sodium salt); D-myo-Inositol-1,4-diphosphate (sodium salt); D-myo-Inositol-1-phosphate (sodium salt); D-myo-Inositol-3,4,5,6-tetraphosphate (sodium salt); D-myo-Inositol-3-phosphate (sodium salt); D-myo-Inositol-4,5-diphosphate (sodium salt); and D-myo-Inositol-4-phosphate (ammonium salt). Variants of 2,3-BPG include, but are not limited to: D-(−)-3-phosphoglyceric acid disodium salt; D-glyceric acid calcium salt dihydrate; and 2,3-diphospho-D-glyceric acid penta(cyclohexylammonium).

Pharmaceutical Formulations, Doses, and Administration: Pharmaceutical compositions for use in accordance with the present invention may be formulated in a conventional manner using one or more physiologically acceptable carriers or excipients.

Any suitable concentration of an active pharmaceutical ingredient may be used, where the active pharmaceutical ingredient is administered in an effective amount to achieve its intended purpose. Determination of a therapeutically effective amount for a particular active ingredient is well within the capability of persons skilled in the art.

The specific therapeutically effective dose level for any particular patient will depend upon a variety of factors including the type and location of the tissue being transplanted; activity of the specific compound employed; the specific composition employed; the age, body weight, general health, sex and diet of the patient; the time of administration, route of administration, and rate of excretion of the specific compound employed; the duration of the treatment; drugs used in combination or coincidentally with the specific compound employed; and like factors well known in the medical arts.

As noted, the delivery can be localized to the affected organ or tissue. Suitable formulations for localized delivery may be topical, injectable or infusible formulations. These formulations may be injected into or infused into the affected organ. For example, where skin is the affected organ, intra-intradermal, subcutaneous administration can be carried out. Likewise, intramuscular injections may be delivered when localized treatment of specific muscles or muscle groups (including those deprived of oxygen due to a medical condition or injury) is required.

Metabolism of a compound (e.g., 2,3-BPG or myo-ITP) may be a concern for these agents. To increase stability, liposomal formulations that deliver a compound as described herein or a functional variant thereof to erythrocytes or bodily tissues (e.g., the skin) may be used. Other approaches to increase the stability of 2,3-BPG within erythrocytes include co-administration of 2,3-BPG, either simultaneously or sequentially (and/or by the same or different routes of administration) with inhibitors of 2,3-BPG phosphatase and/or modulators of 2,3-BPG mutase. Useful inhibitors may include small molecule drugs, peptide or protein therapeutics, or nucleic acids that act through antisense mechanisms or mediate RNAi.

In general, the dose of a compound as described herein may be at least or about 0.01 mg/kg/day to at least or about 1 g/kg/day.

The compounds described herein may be administered directly, and they may also be formulated to include at least one pharmaceutically acceptable carrier, diluent, excipient, adjuvant, filler, buffer, preservative (e.g., benzoic acid or a paraben), lubricant, solubilizer, surfactant, wetting agent, masking agent, coloring agent, flavoring agent, sweetening agent, or any combination thereof. The desired pH of the compositions can be stabilized by a buffer system, non-limiting examples of which include phosphate and citrate buffers.

Also, as described herein, such formulations may also include other active agents, for example, other therapeutic or prophylactic agents. For example, the compositions, methods, and uses of the invention can include an anti-inflammatory agent, an anti-microbial agent (e.g., an antibacterial, anti-fungal, or anti-parasitic agent), a compound that induces epithelialization (e.g., a retinoid), a vitamin (e.g., vitamin D, vitamin C, or vitamin E), a growth factor (e.g., an epidermal growth factor or nerve growth factor) a chelant, trace elements, and/or keratoplastic agents.

Methods of making a pharmaceutical composition include admixing at least one compound, as defined herein, together with one or more other pharmaceutically acceptable ingredients, such as carriers, diluents, excipients, and the like. When formulated as discrete units, such as tablets or capsules, each unit contains a predetermined amount of the active compound, which we may refer to as a unit dosage. Unit dosages can also be applied to a substrate for topical administration.

An acceptable carrier refers to those carriers that cause little or no irritation to the patient, provide suitable preservation if needed, and deliver one or more of 2,3-bisphosphoglycerate, myo-inositol-trispyrophosphate, or a functional derivative thereof in an acceptable and, optimally, homogenous dosage. Pharmaceutically acceptable carriers can include any and all solvents, dispersion media, coatings, isotonic and absorption delaying agents, and the like that are physiologically compatible, sterile aqueous solutions or dispersions and sterile powders for the extemporaneous preparation of sterile injectable solutions or dispersion. The use of such media and agents for pharmaceutically active substances is well known in the art. Supplementary active compounds can also be incorporated into the compositions.

For pulmonary delivery, 2,3-bisphosphoglycerate or a functional variant thereof and/or myo-inositol-trispyrophosphate or a functional variant thereof may be combined with one or more preservatives, co-solvents, surfactants, viscosity enhancers, penetration enhancers, buffers, salts (e.g., sodium chloride), water, or any combination thereof to form an aqueous, sterile suspension or solution that is acceptable for pulmonary delivery.

The formulations may be prepared by any methods known in the art of pharmacy. The formulation may be prepared to provide for rapid or slow release; immediate, delayed, timed, or sustained release; or a combination thereof. Formulations may be in the form of liquids, solutions, suspensions, emulsions, elixirs, syrups, electuaries, mouthwashes, drops, tablets, granules, powders, lozenges, pastilles, capsules, gels, pastes, ointments, creams, lotions, oils, foams, sprays, mists, or aerosols. Formulations may be provided as a patch, adhesive plaster, bandage, dressing, or in the form of depot or reservoir. Many methods for the preparation of such formulations are known to those skilled in the art. In one embodiment, the formulation may be prepared to include any salt or ester containing two phosphate groups such as an ester of pyrophosphoric acid or pyrophosphate.

In certain embodiments, preparation of a sterile ointment formulation can include the combination of the 2,3-bisphosphoglycerate derivatives and/or metabolites and/or myo-inositol-trispyrophosphate derivatives and/or metabolites with a preservative in an appropriate vehicle, such as mineral oil, liquid lanolin, or white petrolatum.

In one embodiment, the active compounds or agents (i.e., 2,3-BPG, myo-inositol trispyrophosphate, or functional derivatives thereof) can be incorporated into liposomes by any known method and the liposomes can then be, optionally, encapsulated (e.g., in bead form). The beads can be formed by suspending the liposomes in a physical and/or physiochemical bonding solution, and can be formulated for slow- or controlled release. The bonding solution can contain at least one organic compound such as agarose, a cellulose, sodium alginate, a chitosan, a polymeric substance, or another compound having characteristics suitable for achieving physical or physiochemical bonding (or any mixture or combination of such compounds). This solution can then be introduced into a second solution containing an inorganic salt (e.g., from about 1 to 2% by weight of an inorganic salt). The effect of the interaction of the solutions is to harden the outermost, exposed areas of the introduced liposome solution. The inorganic salt can be, for example, calcium chloride or sodium hydroxide, although other types of inorganic salts can be used such as calcium sulfate, calcium carbonate, magnesium chloride, magnesium sulfate, barium chloride, barium sulfate and the like. A difficulty, particularly with regard to 2,3-BPG, is that it is poorly absorbed across the plasma membranes of red blood cells. Accordingly, the invention features compositions, methods, and uses of that compound and functional derivatives thereof that are formulated for increased absorption. These compositions, methods, and uses can be employed whether the target is an erythrocyte or a cell within a tissue in vivo or ex vivo. In addition to liposomes and beads (e.g., sustained-release beads), 2,3-BPG or myo-ITP, and/or functional variants thereof can be formulated into microspheres, gauzes or dressings (as described further herein), polymerized threads or ropes, meshes, gels, suspensions, ointments, or solutions, any of which can include bioabsorbable or inert compounds that can be applied topically to the skin, a wound, a tissue, or tissue bed.

As noted, the present compositions, methods, and uses include formulations for topical administration or use (e.g., to the surface of the skin, to a wound bed or other breach of the skin or membranous tissue, or to the surface of any other bodily part (e.g., an articular space). Such formulations can include, in addition to 2,3-BPG, myo-ITP, or a functional variant thereof, any of the carriers generally considered suitable for topical formulations, including but not limited to, water, glycerol, vegetable or mineral oils, white petrolatum (white soft paraffin), mild detergents, branched chain fats or oils, animal fats, alcohol, high molecular weight alcohols (greater than $C_{12}$) or solvents such as propylene glycol optionally mixed with one or more preservatives, absorption promoters, emulsifiers, stabilizers and/or antioxidants, as well as agents imparting color or fragrance if desired.

Gels generally contain a high concentration of water and yet are solid or semi-solid in appearance. They can entrap the compounds described herein and be configured to release them slowly or over a given period of time. The compounds described herein can be formulated in a hydrogel, and that hydrogel can be incorporated into a dressing (e.g., a non-adhering hydrogel dressing that can be placed directly on, for example, a wound bed to maintain a moist wound surface). Accordingly, the invention encompasses a dressing including a substrate to which or on which a hydrogel containing 2,3-BPG, myo-ITP, or a functional variant thereof has been adhered (we may refer to such a dressing as a hydrogel sustained release dressing). The dressing can include a protective film that is fully or partially occlusive (air- and water-proof or air- and water-repellent), and the film may be removable such that the dressing can be made permeable. An adhesive surface can be positioned, for example, around the periphery of the dressing, on the side or planar surface of the dressing configured to contact the patient's skin (or other organ). The hydrogel component can be made by methods known in the art. For example, a gelatinous hydrogel can be formed by adding gelatin to water that is sufficiently hot to dissolve the gelatin. 2,3-BPG, myo-ITP, or a functional variant thereof, together with any other component of the present compositions can then be added at a suitable temperature prior to gelling. When the solution is then cooled, submicroscopic crystalline particle groups that retain a great deal of water in the interstices are formed. The gels can be formed from naturally occurring or synthetic materials or from a combination of the two. Other pharmaceutically acceptable gelling substances can be used and methods that can be used to incorporate the present compounds in such formulations are known to one of ordinary skill in the art. Materials within the dressings of the invention can be bioabsorbable and/or inert material that could be removed.

Further, the present compounds (2,3-BPG, myo-ITP, and functional variants thereof) can be incorporated into a cultured, synthetic skin (a skin substitute or skin restorative) that is applied to a wound bed in a manner similar to affixing a skin graft. Accordingly, the invention encompasses such artificial skins or skin substitutes, which can include cell bi-layers; a layer to be positioned externally that includes protective skin cells and a layer to be positioned internally (nearest the patient) including cells within a matrix (e.g., a collagen or extracellular matrix substance). This material can also include any of the additional therapeutic agents described herein (e.g., an anti-inflammatory agent, an antimicrobial agent, and growth factors). For example, the present compounds could be incorporated into Apligraf®.

The formulations described herein may also contain an ingredient that improves the penetration of an active compound therein. Such ingredients may be naturally occurring or synthetic and are well known to one of ordinary skill in the art. They include, for example, surfactants (see, Som et al., *J. Pharm. Bioallied Sci.* 4(1):2-9, 2012) and the penetration-enhancing diol or cycloketo compounds described in EP 0129284 (e.g. 1,2-propanediol, 1,3-propanediol, 1,2-butanediol, 1,3-butanediol, 1,4-butanediol, or 2,3-butanediol). See also, Ganesh et al. (*Intl. Research J. Pharm.* 3(5):82-88, 2012).

Routes of Administration: In certain embodiments, pharmaceutical compositions of the present invention may be formulated for administration by any route of administration, including but not limited to systemic, peripheral, or topical. Illustrative routes of administration include, but are not limited to, oral, such as by ingestion, buccal, sublingual, transdermal including, such as by a patch, plaster, and the like, transmucosal including, such as by a patch, plaster, and the like, intranasal, such as by nasal spray, ocular, such as by eye drops, pulmonary, such as by inhalation or insufflation therapy using, such as via an aerosol through the mouth or nose, rectal, such as by suppository or enema, vaginal, such as by pessary, parenteral, such as by injection, including subcutaneous, intradermal, intramuscular, intravenous, intraarterial, intracardiac, intrathecal, intraspinal, intracapsular, subcapsular, intraorbital, intraperitoneal, intratracheal, subcuticular, intraarticular, subarachnoid, and by implant of a depot or reservoir, such as intramuscularly. Methods of preparing pharmaceutical formulations are well known in the art. Dosage of the pharmaceutical compositions may vary by route of administration. Certain administration methods may include the step of administering the composition one or more times a day to obtain the desired therapeutic effect.

Where the present compounds are topically applied or applied to the surface or a body part or organ, it is likely that some amount of the compound will be absorbed through the capillaries that permeate the tissue and effect oxygen release from RBCs. However, a substantial amount will be directly absorbed by the tissue itself. The compounds within the compositions, methods, and uses of the invention may therefore have effects through additional mechanisms including a "nutritive effect" on the damaged tissue that is unrelated to the effect on RBCs.

While the invention is not limited with regard to any particular mechanism of action, while both 2,3-BPG and myo-ITP are known to facilitate the release of oxygen from hemoglobin, myo-ITP can be converted by phosphatase enzymes into myo-inositol, which is considered a member of the Vitamin B complex but is not an essential nutrient. While we assume that the biologic effect of these compounds is in part due to the facilitation of the release of oxygen, there are possibly other nutrient effects that may be beneficial to wound healing that are wholly unrelated to RBCs, blood, circulation, and etc. In regards to 2,3-BPG, the enzyme 2,3 bisphosphoglycerate phosphatase converts the 2,3-BPG into 3-phosphoglycerate. 3-phosphoglycerate is a precursor for the non-essential amino acid serine. So, in addition to this compound's effects on oxygen release, it may have other direct and/or indirect nutritional effects on tissue either directly or indirectly via catabolic products.

Any of the compositions, methods, and uses of the present invention can be optimized in an animal model. For example, to model a wound in a human patient, one could use an animal burn model as described in *Acta Cir. Bras.* 14(4) São Paulo October/December 1999. Experimental burns can also be induced in rodents, such as rats or mice, or other animals such as pigs according to approved protocols. Summarily, following the creation of experimental burns, solutions of placebo vehicle (saline), 0.1% myo-inositol triphosphate, 1.0% myo-inositol triphosphate, 0.1% 2.3-diphosphoglycerate, 1.0% di-phosphoglycerate can be applied every 8 hours for 14 days. Skin biopsy specimens from the burn sites can be obtained from each of the animals at baseline, 3 days, 7 days, 10 days, 14 days, 21 days, and 28 days and submitted for routine histologic analysis. These samples can be used to quantitate improvements in overall wound healing time, the rate of cutaneous re-epithelization, scar tissue formation, acute and chronic inflammatory responses, and collagen and connective tissue formation.

What is claimed is:

1. A method of treating skin ulcers, diabetic skin ulcers, venous stasis skin ulcers, decubitus ulcers, burns, or chronic skin wounds in a patient in need thereof, the method comprising administering, to the patient, a therapeutically effective amount of myo-inositol trispyrophosphate, or a functional variant thereof.

2. A method of enhancing oxygen delivery to peripheral tissue, the method comprising administering, to a patient having a skin ulcer, a diabetic skin ulcer, a venous stasis skin ulcer, a decubitus ulcer, a burn, or a chronic skin wound, a therapeutically effective amount of myo-inositol trispyrophosphate, or a functional variant thereof.

3. The method of claim 1, wherein the therapeutically effective amount of myo-inositol trispyrophosphate, or a functional variant thereof comprises an excipient further comprising a solvent, diluent, vehicle, dispersion or suspension aid, surface active agent, isotonic agent, thickening or emulsifying agent, preservative, solid binder, lubricant or any combination thereof.

4. The method of claim 1, wherein the therapeutically effective amount of myo-inositol trispyrophosphate, or a functional variant thereof further comprises a liposome.

5. The method of claim 1, wherein the therapeutically effective amount of myo-inositol trispyrophosphate, or a functional variant thereof is topically administered.

6. The method of claim 1, wherein the therapeutically effective amount of the myo-inositol trispyrophosphate is 1.0%-0.1% (wt.).

7. The method of claim 2, wherein the therapeutically effective amount of the myo-inositol trispyrophosphate is between 1.0%-0.1% (wt.).

8. The method of claim 2, wherein the patient is having a diabetic skin ulcer.

9. The method of claim 2, wherein the therapeutically effective amount of myo-inositol trispyrophosphate, or a functional variant thereof further comprises a liposome.

10. The method of claim 1, wherein the myo-inositol trispyrophosphate, or a functional variant thereof is administered topically.

11. The method of claim 2, wherein the myo-inositol trispyrophosphate, or a functional variant thereof is administered topically.

12. The method of claim 1, wherein the myo-inositol trispyrophosphate, or a functional variant thereof is formulated as a liquid, solution, suspension, emulsion, elixir, syrup, electuary, mouthwash, drop, tablet, granule, powder, lozenge, pastille, capsule, gel, paste, ointment, cream, lotion, oil, foam, spray, mist, aerosol salve, a bandage, dressing, patch, foam dressing, silicone gel dressing, antimicrobial silver dressing, or a hydrogel dressing.

13. The method of claim 2, wherein the myo-inositol trispyrophosphate, or a functional variant thereof is formulated as a liquid, solution, suspension, emulsion, elixir, syrup, electuary, mouthwash, drop, tablet, granule, powder, lozenge, pastille, capsule, gel, paste, ointment, cream, lotion, oil, foam, spray, mist, aerosol salve, a bandage, dressing, patch, foam dressing, silicone gel dressing, antimicrobial silver dressing, or a hydrogel dressing.

14. The method of claim 1, wherein the myo-inositol trispyrophosphate, or a functional variant thereof is administered localized to the affected organ or tissue.

15. The method of claim 2, wherein the myo-inositol trispyrophosphate, or a functional variant thereof is administered localized to the affected organ or tissue.

16. The method of claim 1, wherein the myo-inositol trispyrophosphate, or a functional variant thereof is formulated to provide for rapid or slow release; immediate, delayed, timed, or sustained release; or a combination thereof.

17. The method of claim 2, wherein the myo-inositol trispyrophosphate, or a functional variant thereof is formulated to provide for rapid or slow release; immediate, delayed, timed, or sustained release; or a combination thereof.

18. The method of claim 1, wherein the myo-inositol trispyrophosphate, or a functional variant thereof is administered by a route of administration selected from the group consisting of oral, transdermal, transmucosal, intranasal, ocular, pulmonary, rectal, vaginal, injection, or via a device selected from the group consisting of patch, adhesive plaster, bandage, dressing, or in the form of depot or reservoir, or an implant of a depot or a reservoir.

19. The method of claim 2, wherein the myo-inositol trispyrophosphate, or a functional variant thereof is administered by a route of administration selected from the group consisting of oral, transdermal, transmucosal, intranasal, ocular, pulmonary, rectal, vaginal, injection, or via a device selected from the group consisting of patch, adhesive plaster, bandage, dressing, or in the form of depot or reservoir, or an implant of a depot or a reservoir.

20. The method of claim 1, wherein the myo-inositol trispyrophosphate, or a functional variant thereof is administered in combination with one or more additional active pharmaceutical ingredients.

21. The method of claim 2, wherein the myo-inositol trispyrophosphate, or a functional variant thereof is administered in combination with one or more additional active pharmaceutical ingredients.

* * * * *